United States Patent [19]

Mulder

[11] 4,384,956

[45] May 24, 1983

[54] WASTE WATER PURIFICATION

[75] Inventor: Arnold Mulder, Apeldoorn, Netherlands

[73] Assignee: Gist-Brocades N.V., Delft, Netherlands

[21] Appl. No.: 317,585

[22] Filed: Nov. 3, 1981

[30] Foreign Application Priority Data

Nov. 7, 1980 [NL] Netherlands .......................... 8006094

[51] Int. Cl.$^3$ .............................. C02F 3/28; C02F 3/30
[52] U.S. Cl. ..................................... 210/603; 210/605; 210/610; 210/631; 210/903
[58] Field of Search ................ 210/903, 605, 603, 630, 210/631, 622, 623, 626, 611, 610; 55/68, 73; 48/197 A

[56] References Cited

U.S. PATENT DOCUMENTS

| | | | |
|---|---|---|---|
| 3,829,377 | 8/1974 | Hashimoato | 210/603 |
| 4,134,830 | 1/1979 | Skogman et al. | 210/605 |
| 4,183,809 | 1/1980 | Klapwijk et al. | 210/605 |

FOREIGN PATENT DOCUMENTS

| | | | |
|---|---|---|---|
| 139248 | 12/1979 | Fed. Rep. of Germany | 210/605 |
| 51-8754 | 1/1976 | Japan | 210/605 |
| 52-52466 | 4/1977 | Japan | 210/903 |
| 53-90192 | 8/1978 | Japan | 210/611 |

Primary Examiner—Benoit Castel
Attorney, Agent, or Firm—Hammond & Littell, Weissenberger and Muserlian

[57] ABSTRACT

A novel process for the purification of waste water and/or waste water sludge comprising subjecting the waste water and/or waste water sludge to first a methane fermentation step, then a denitrification step and finally an oxidation step by aeration, the electron donor in the denitrification step being mainly the sulfide from the methane fermentation step and the remaining reduced compounds in the liquid effluent from the methane fermentation step being oxidized in the aeration step.

5 Claims, 2 Drawing Figures

WASTE WATER PURIFICATION

STATE OF THE ART

The purification of waste water and/or waste water sludge by subjecting the same to methane fermentation and oxidizing the reduced components in the liquid effluent of the methane fermentation by aeration is generally known and is especially used for treatment of waste water and/or waster water sludge of fermentation industries (Sew.W.J. 1948, 1084 and 1949, 1000, 294, 491, 700, 1028 and Ind. Eng. Chem. 1949, 1535).

In the first stage of such a process, the COD present in the waste water or sludge is converted for the most part into methane and carbon dioxide, while hydrogen sulfide and ammonia originate fron the sulfur containing compounds and nitrogen containing compounds, respectively. The hydrogen sulfide is partially found in the methane gas and must be removed therefrom before the methane gas can be used for energy production, while the residue of the hydrogen sulfide is found in the liquid effluent of the methane fermentation in the form of insoluble precipitates and dissolved $H_2S$ and/or $HS^-$ions. The ammonia dissolves mainly in the liquid effluent of the methane fermentation. Therefore, the liquid effluent of the methane fermentation is not appropriate for a direct disposal as it smells and is toxic.

In the second stage, the organic dissolved compounds in the effluent are partially degraded with aeration or are converted into sludge which is removed and, for instance, is recirculated to the methane fermentation through which the COD of that effluent significantly decreases and the sulfides and ammonia are oxidized into sulfate ions and nitrate ions, respectively. The said nitrate gives rise to problems with eutrofication of surface water with disposal of the aerated water if waste and or waste water sludge having a high content of nitrogen containing compounds are used. Therefore, the nitrate in the aerated effluent of the methane fermentation is converted under practical conditions into nitrogen in the usual way [see for instance J.A.W.W.A., 659–669 (1969)] under anaerobic conditions in the presence of naturally occurring denitrificating microorganisms and by use of organic compounds such as methanol as electron donor in a so-called denitrification whereby the obtained nitrogen is removed.

In such an operation, several difficulties are connected with waste water and/or waste water sludge which contains many sulfur-containing impurities, namely (1) In the aeration reactor, a large amount of oxygen is necessary for the oxidation of $H_2S/HS^-$ and air which is blown into this reactor for the oxygen supply is strongly polluted with $H_2S$ and other strong odor components, for instance in the form of mercaptans, which makes post treatment of this air required.

(2) The sulfate formed in the aeration step is reconverted into sulfide during the anaerobic denitrification with all the problems connected with it, such as inhibition of the denitrification at a low sulfide concentration of 1 mg/l.

(3) The methane gas has to be treated separately for removal of $H_2S$.

(4) At varying $NO_3^-$ concentrations, the COD depletion into the nitrate reducing reactor forms a serious problem.

(5) The final waste water is oxygen-free and contains toxic sulfides and a possible excess of COD from the denitrification step.

OBJECTS OF THE INVENTION

It is an object of the invention to provide an improved process for the treatment of waste water and/or waste water sludge while avoiding the problems of sulfide and nitrate disposal.

It is a further object of the invention to provide a waste water and/or waste water sludge purification using sulfide from methane fermentation effluent as the electron donor in the denitrification step.

These and other objects and advantages of the invention will become obvious from the following detailed description.

THE INVENTION

The novel process of the invention for the purification of waste water and/or waste water sludge comprises subjecting the waste water and/or waste water sludge to first a methane fermentation step, then a denitrification step and finally an oxidation step by aeration, the electron donor in the denitrification step being mainly sulfide from the methane fermentation step and the remaining reduced compounds in the liquid effluent from the methane fermentation step being oxidized in the aeration step.

Surprisingly, it was found that the prior art problems are significantly diminished or even completely avoided when the sulfide from the effluent of the methane fermentation step is used as the electron donor in the denitrification step and when the remaining reduced compound from the liquid effluent of the methane fermentation are only then oxidized by aeration. In this way, the sulfides are used in an appropriate way and are simultaneously converted into non-interfering sulfates by the following reaction:

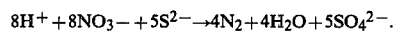

$$8H^+ + 8NO_3^- + 5S^{2-} \rightarrow 4N_2 + 4H_2O + 5SO_4^{2-}.$$

Ammonia is still present in the liquid effluent remaining after the denitrification which ammonia was in the effluent of the methane fermentation and this ammonia is subsequently oxidized into nitrate ions by the aeration which the sulfide ions cannot disturb as the sulfide ions were converted into $SO_4^{2-}$ in the denitrification step. As sulfide ions are no longer present, the aeration step requires less air and the aeration will be more simple.

It will be appreciated that the possibility of the denitrification using sulfur-containing compounds in a reduced state as compared to the $SO_4^{2-}$ state such as $S^{2-}$, $S$, $S_2O_3^{2-}$, $S_4O_6^{2-}$, $SO_3^{2-}$ as the eletron donor and the application of *Thiobacillus denitrificans* as a microorganism is known from Batchelor and Lawrence, "Chemistry of Wastewater Technology", chapter 24. But the use of a liquid effluent from a methane fermentation of waste water with many sulfur containing impurities as a source for sulfides to serve as electron donor is not known at all and even the possibility of reaching great advantages with such an effluent cannot be derived therefrom.

The hydrogen sulfide from the gas which is formed in the methane fermentation step also can serve as an electron donor in the denitrification step and is preferably used for this purpose. In this way, the greatest profit of the products obtained from the methane fermentation is realized while the gas is additionally purified in a simple way.

If the S/N-ratio, which is obtained in that way, is insufficient to reduce all $NO_3$-ions, unpurified waste water containing sufficient amounts of COD is introduced into the denitrification reactor to reduce the introduced nitrate to $N_2$ as completely as possible. If an excess of COD in the denitrification reactor is used due to variations in nitrogen and sulfur concentrations in the waste water, this excess is automatically oxidized to carbon dioxide in the next aeration step so the COD does not give rise to decreased purification.

The nitrate containing effluent formed in the aeration step and in which sulfur compounds such as $SO_4^{2-}$ are present may suitably serve as nitrate containing waste water for the denitrification. That is why the nitrate containing effluent formed during the aeration is partially subjected to denitrification as a nitrate containing waste water of the invention and whereby the residue is disposed of. During the denitrification step, the sulfate ions do not interfere and they are not reduced themselves as the sulfide ions are used for the denitrificating reduction which sulfide ions are not able to reduce the sulfate ions.

In this way, an integrated system is obtained whereby the effluent of the methane fermentation step of waste water and/or waste water sludge is first used as a sort of electron donor for denitrification, the effluent of the denitrification is aerated with formation of nitrate ions and the nitrate containing liquid is added to the denitrification step.

It will be appreciated from chapter 15 of "Nitrification and Denitrification in Waste Water Treatment" that an integration of a denitrification step and a nitrification step is well known but in the therein disclosed system unpurified waste water is used as a source of an electron donor in the denitrification and is combined with nitrate containing waste water obtained by aeration of the effluent of the denitrification step. The use of the liquid effluent of the methane fermentation step of many sulfur compound-containing waste water and/or waste water sludge as a source of an electron donor in the denitrification step cannot be derived therefrom.

With the integrated process of the invention, a purification of waste water and/or waste water sludge containing nitrogen and sulfur impurities is obtained, whereby due to the methane fermentation of the COD of the waste water and/or the waste water sludge methane gas is recovered which may be used as a source of energy and due to the use of the liquid effluent and the gas of the methane fermentation as a source of $H_2S$, $HS^-$ and/or $S^{2-}$ which serve as electron donor for the denitrification step, a reproducible, economical removal of nitrogen and reduced sulfur compounds is obtained.

The total amount of nitrogen which is removed depends on the volume ratio between the nitrate containing effluent subjected to the denitrification step, and the effluent of the methane fermentation which is used in the denitrification step. Preferably, this volume ratio is at least 1:1 and, in this case, at least 50% of the nitrogen is removed. Preferably, the ratio is 4:1 to 9:1, because the amount of nitrogen, calculated on basis of the waste water and/or waste water sludge, which is removed will be optimum for all practical purposes with ratios between these limits, namely 80 to 90%.

Due to the high volume ratios of 4:1 to 9:1, the flow rate of the water through the denitrification reactor and nitrification reactor increases tremendously. Therefore one or more of these steps of this process are carried out preferably in a so-called biologically fluidized bed reactor, wherein the biomass grows attached to a solid heavy carrier and thus is not leaving the reactor under high flow rate conditions. More preferably in the denitrification such system is used. Such a biomass attached to a heavy carrier system may be obtained e.g. by a process of the copending patent application Ser. No. 182.068 filed Aug. 28, 1980, the relevant parts of which are considered as integrally inserted herein.

Referring now to the drawings

Figure 1:
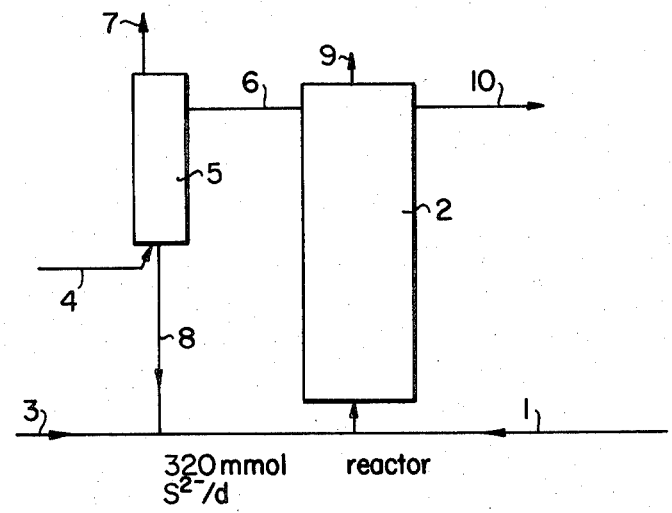
FIG. 1 is a schematic illustration of the basic process of the invention.

In FIG. 1, nitrate containing waste water is supplied by line 1 to denitrification reactor 2 having an upgoing liquid flow (up-flow reactor) and liquid effluent of the methane fermentation of waste water and/or waste water sludge containing nitrogen and sulfur impurities is pumped by line 3 to reactor 2. Hydrogen sulfide containing gas from the methane fermentation is pumped by line 4 into the bottom of an absorption column 5 and in the upper part thereof, the liquid effluent from denitrification reactor 2 is supplied through line 6. The methane gas from which hydrogen sulfide has been removed in this way is collected from the absorption column 5 via line 7.

The liquid in which hydrogen sulfide is absorbed leaves absorption column 5 by line 8 and is added to the liquid effluent of the methane fermentation in line 3. In the denitrification reactor 2, nitrate ions are reduced to nitrogen which is collected by line 9. From the top of the denitrification reactor 2, an amount of purified waste water is drained off by line 10 and this amount of purified waste water is equal to the amount of nitrate containing waste water supplied by line 1 together with the amount of liquid effluent from the methane fermentation supplied by line 3.

Figure 2:
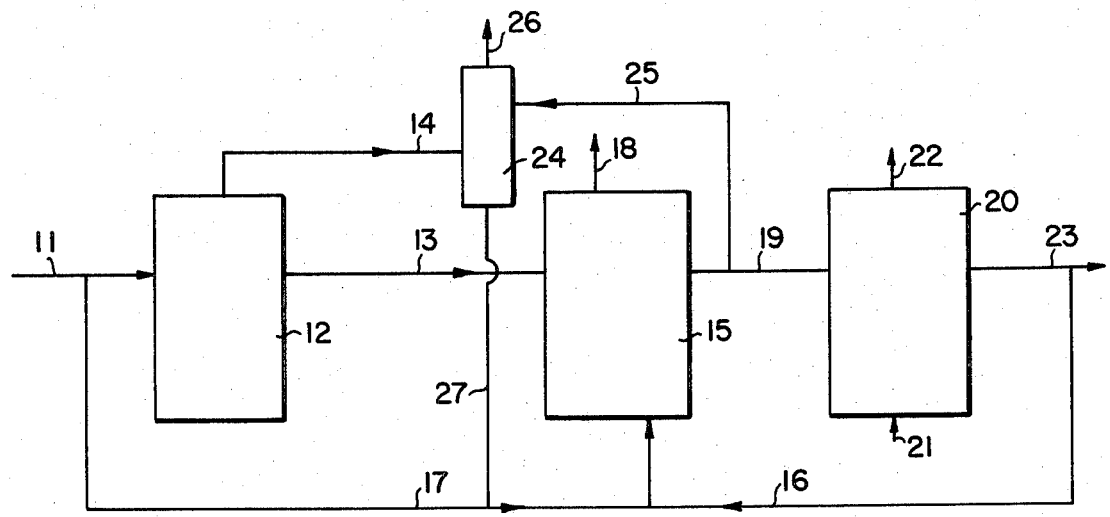
FIG. 2 is a schematic flow sheet of a preferred embodiment of the invention.

In FIG. 2, the waste water and/or waste water sludge containing COD, nitrogen and sulfur compounds is supplied by line 11 to a methane fermentation reactor 12 from which ammonia and sulfide containing liquid effluent is supplied by line 13 to a denitrification reactor 15, to which nitrate containing waste water from the subsequent aeration stage is added by line 16 and non-purified COD containing waste water from line 11 is added by pipeline 17.

A gas stream containing carbon dioxide, methane and hydrogen sulfide formed in the methane fermentation step is supplied by line 14 to a scrubber column 24 wherein the hydrogen sulfide is removed from the gas by washing with denitrified waste water supplied by line 25. The gas from which hydrogen sulfide has been removed is collected from column 24 by line 26 and the wash liquid in which hydrogen sulfide has been absorbed is led by line 27 into line 17 and from there to the denitrification reactor 15. In the denitrification reactor, the nitrate ions present in the liquid mixture are reduced to nitrogen which is collected by line 18. Denitrified effluent containing ammonia originally from the effluent of the methane fermentation and sulfate ions formed by the denitrification from sulfide is led to an aerobic reactor 20 by line 19. To this aerobic reactor 20, oxygen for the oxidation of the ammonia is supplied by line 21. The carbon dioxide and the remaining air obtained after the oxidation of the COD is collected by line 22. Nitrified effluent leaves the reactor 20 by line 23 and a part of this effluent is discharged as purified water with the remaining part being recirculated by line 16 to denitrification reactor 15.

In the following examples there are described several preferred embodiments to illustrate the invention. However, it should be understood that the invention is not intended to be limited to the specific embodiments.

EXAMPLE 1

The apparatus of FIG. 1 was used in the experiment and reactor 2 had a height of 1.1 meters and a diameter of 0.09 meters for a total volume of 6.5 liters. As aqueous nitrate solution containing 400 mg of nitrate nitrogen per liter was introduced by line 1 into reactor 2 at a rate of 40 liters per day which was equivalent to 1140 mg of $NO_3^-$ per day. 40 liters per day of liquid effluent containing 240 mg of sulfur per liter from a methane fermentation reactor were added to reactor 2 by line 3. The corresponding gas from the methane fermentation was introduced by line 4 into the bottom of absorption column 5 and was passed through to the liquid from denitrification reactor 2 introduced by line 6 at the top of column 5 whereby hydrogen sulfide was removed from the gas. The purified methane gas was recovered by line 7 and the liquid from the bottom of the column was mixed by line 8 with the liquid effluent in line 3 for adding to reactor 2.

The liquid in denitrification reactor 2 was stirred at 2 rpm at 20° to 30° C. at a pH of 7.3-7.4 and the effluent in line 10 contained a negligible amount of nitrate ions and 400 mg of sulfate ions per liter. The denitrification gas recovered by line 9 was about 7 liters per day and consisted of 80% of nitrogen and 20% of carbon dioxide. The presence of carbon dioxide indicates that the nitrification also took place with COD in the waste water but the high nitrogen content of the gas and the high sulfate ion concentration in the effluent of line 10 show that the sulfides were the dominant electron contributor to the denitrification. A denitrification capacity of 1.2 kg of $NO_3^-$ nitrogen per cubic meter reactor per day was achieved.

EXAMPLE 2

The apparatus of FIG. 2 was used in this experiment and methane fermentation reactor 12 had an effective volume of 35 liters, denitrification reactor 15 had an effective volume of 6.5 liters and aerobic reactor 20 had an effective volume of 13 liters which combined with a settler to prevent sludge from being carried away with the nitrificated effluent provided a total volume of 23 liters.

The methane fermentation reactor 12 was prepared for the experiment by passing waste water containing COD, nitrogen compounds and sulfur compounds therethrough at a rate of 50 liters per day for 3 months after which the reactor contained 330 g of sludge, calculated as organic material.

The denitrification reactor 15 was prepared by filling it half way with active sludge from the aeration basin of the municipal waste water treatment plant of Renkum-Wageningen, Netherlands, and the rest of the reactor was filled with effluent from methane fermentation reactor. After two days, 2 liters of liquid were replaced with fresh effluent from the methane fermentation reactor and the said process was repeated for one month. Then, the effluent from the fermentation reactor was continuously added to reactor 15 at a rate of 10 liters per day which rate was regularly increased over a month to a rate of 50 liters per day which was equivalent to a residence time of 3.1 hours in the reactor.

Nitrification reactor 20 was prepared by introducing 7.5 liters of sludge from the aeration basin of the said municipal plant so that the reactor contained 50 g of sludge, calculated as organic material.

After the said three reactors were thus prepared, the test was begun by introducing water containing COD, nitrogen compounds and sulfur compounds by line 11 into the methane fermentation reactor 12 at a rate of 50 liters per day and the liquid effluent therefrom was continuously added by line 13 to denitrification reactor 15. The gas from reactor 12 was passed by line 14 to gas scrubber 24 and a portion of the liquid effluent from reactor 15 was introduced by line 25 into the scrubber 24. The liquid effluent from scrubber 24 was passed by line 27 for admixture with waste water in line 17 and then passed into reactor 15. The washed methane gas was recovered by line 26. The remaining effluent from reactor 15 was passed by line 19 to aeration reactor 20 and the liquid effluent from reactor 20 was recycled by line 16 to denitrification reactor 15. When the system was completely filled, the system was run for one month with removal of effluent from reactor 20 by line 23 equal to the volume of waste water added by line 11 to obtain a steady state condition.

The prevailing conditions reached in each reactor after establishment of equilibrium conditions I are reported in Table A and the composition of the waste water added at line 11 and of the various effluents are reported in Table B. Table C represents the amounts and composition of the gases collected from the methane fermentation reactor and the denitrification reactor.

Then, the waste water addition at line 11 was increased to 51 liters per day and the composition of the waste water changed as well as the other effluent flow rates. The recycled effluent in line 16 was admixed with a sufficient volume of a sodium nitrate solution (not shown in FIG. 2) to avoid recycling too much of the effluent from reactor 20. Equilibrium conditions II were reached after one month and the said volumes are also reported in Tables A, B and C.

TABLE A

| | Process conditions | | | | | |
|---|---|---|---|---|---|---|
| | Reactor 12 | | Reactor 15 | | Reactor 20 | |
| | I | II | I | II | I | II |
| effective vol. (l) | 35 | 35 | 6.5 | 6.5 | 13 | 13 |
| amount of sludge (g. org. material) | 330 | 330 | 66 | 66 | 50 | 50 |
| average temp.: °C. | 37 | 37 | 25.5 | 25.5 | 23 | 23 |
| pH | 7.2 | 7.2 | 8.2 | 8.2 | 7.8 | 7.8 |
| recirc. through pipeline 16 in l/d | | | 42 | 63.5 | 42 | 63.5 |
| residence time in h | 16.8 | 16.5 | 3.1 | 3.1 | 6.2 | 6.1 |

TABLE B

| | Composition of liquid streams | | | | | | | |
|---|---|---|---|---|---|---|---|---|
| in line | 11 | | 13 | | 19 | | 16/32 | |
| situation | I | II | I | II | I | II | I | II |
| $SO_4^=$ mg/l | 586 | 1374 | 1 | 2 | 293 | 608 | 285 | 628 |
| sulfide (mg/l as S) | — | — | — | 378 | — | — | — | — |
| COD mg/l | 3510 | 6700 | 835 | — | — | — | 545 | 1115 |
| $NH_4^+$ (mg/l as N) | 272 | — | 403 | 295 | — | 141 | 159 | 51 |
| nitrite (mg/l as N) | — | — | — | — | — | 0 | 30.2 | 41.1 |
| nitrate | | | | | | | | |

TABLE B-continued

| in line | Composition of liquid streams | | | | | | | |
|---|---|---|---|---|---|---|---|---|
| | 11 | | 13 | | 19 | | 16/32 | |
| situation | I | II | I | II | I | II | I | II |
| (mg/l as N) | — | — | — | — | — | — | 46 | 50 |
| added nitrate in pipeline 16 (g/d as NO$_3$−) | | | | | | | | 11 |

TABLE C

| liters per day of gas measured at stand. temp. and pressure | Amount of gas formed and gas composition | | | |
|---|---|---|---|---|
| | in line 14* | | in line 18 | |
| | I | II | I | II |
| | 55 | 102.6 | 2.98 | 7.14 |
| N$_2$ | 2.9 | 1.5 | 85.9 | 85.2 |
| O$_2$ | 0.34 | — | 1.9 | — |
| CH$_4$ | 73.4 | 67.7 | 8.6 | 7.9 |
| CO$_2$ | 19.9 | 26.3 | 3.2 | 4.3 |

*after removal of H$_2$S

The results of Tables A, B and C show that under variable conditions an efficient denitrification can be reached without problems in waste water in which sulfur compounds are present by the present invention. It follows from the amounts of sulfur compounds in the various streams that in these experiment losses of sulfur have appeared and various causes can be indicated: (a) some sulfide is lost with the gas of the methane fermentation; (b) during the process some FeS is formed which is not expressed in the sulfur balance; and (c) in places where oxygen is present (tube connections, head of the reactor), formation of elementary sulfur takes place which also does not appear in the sulfur balance.

EXAMPLE 3

The following experiment was carried out in an equipment according to FIG. 1. In this particular experiment however there was no H$_2$S-stripping of the biogas involved. This means that the gasflow through the pipes 4 and 7 was 0. The recirculation of water through the pipes 6 and 8 was however maintained at 600 l/hr.

The reactor 2 had a height of 12 m, 0.2 m diameter and had a volume of 400 ltr. This reactor was loaded at the start of the experiment with 100 kg sand of 0.8–1.2 mm particle diameter. This sand was maintained in the fluidized state with sufficient recirculation waterflow through pipes 6 and 8 as mentioned above.

A nitrate containing solution (333 gr NaNO$_3$/kg) was fed in the reactor 2 through pipe 1 at a rato of 1 ltr/hr.

Through pipe 3 a 350 ltr/hr of anaerobic, sulfide containing stinking waste water (originated from a waste water methane reactor) was fed into reactor 2. The sulfide concentration in this waste water was about 150 mg S$_2$−/ltr. The pH of reactor 2 was maintained at 7.6–7.8 and the temperature was maintained at 350° C.

The biomass concentration in the biomass coated sand fluidized bed in reactor 2 was about 35–40 gr USS/kg.

The purified, odourless waste water flowing through line 10 contained about 450 mg SO$_4^{2-}$/ltr. The gas production through pipe 9 averaged about 1200 l/day and the composition was 65% N$_2$, 20% CH$_4$, 15% CO$_2$. The denitrification capacity can thus be estimated at 2.5 kg N/m$^3$ reactor day.

Various modifications of the process of the invention may be made without departing from the spirit or scope thereof and it is to be understood that the invention is intended to be limited only as defined in the appended claims.

What I claim is:

1. A process for the purification of waste water rich in organic substances and containing substantial amounts of nitrogen compounds and sulfur compounds and optionally present recycled activated waste water sludge comprising subjecting the waste water and optionally present recycled activated waste water sludge to a first anaerobic fermentation step to produce an off gas containing gaseous methane, ammonia and hydrogen sulfide and an aqueous phase containing dissolved sulfide, recovering said gaseous hydrogen sulfide from said off gas produced in the anaerobic fermentation step and adding it to said aqueous phase from said anaerobic fermentation step, subjecting the said aqueous phase and an aqueous stream rich in nitrates, where the volume ratio of the aqueous stream rich in nitrates to said aqueous phase containing added hydrogen sulfide is at least 1:1, to an anaerobic biological denitrification step to produce nitrogen from nitrates in said aqueous stream rich in nitrates and biologically oxidizing the resulting aqueous effluent from said denitrification step by aeration to form nitrate ions from ammonia and carbon dioxide from the organic substances in the aqueous effluent, whereby the added gaseous hydrogen sulfide and the dissolved sulfide act as electron donors for the nitrate reduction during the denitrification step.

2. The process of claim 1 wherein a portion of the nitrate containing effluent from the aeration step is recycled to the denitrification step.

3. The process of claim 1 wherein the volume ratio is 4:1 to 9:1.

4. The process of claim 3 wherein activated sludge is employed in the denitrification step and is attached to a solid heavy carrier which prevents its removal at high flow rates.

5. The process of claim 1 wherein the off gas produced in the first anaerobic fermentation step is passed through a gas scrubber to recover said gaseous hydrogen sulfide.

* * * * *